US012465338B2

(12) United States Patent
Nelson et al.

(10) Patent No.: US 12,465,338 B2
(45) Date of Patent: Nov. 11, 2025

(54) VACUUM-ASSISTED SOFT TISSUE BIOPSY DEVICE

(71) Applicant: Merit Medical Systems, Inc., South Jordan, UT (US)

(72) Inventors: Nathan Otis Nelson, South Jordan, UT (US); John Robert Durham, Cottonwood Heights, UT (US); Michael Hallisey, Old Saybrook, CT (US)

( * ) Notice: Subject to any disclaimer, the term of this patent is extended or adjusted under 35 U.S.C. 154(b) by 856 days.

(21) Appl. No.: 17/648,263

(22) Filed: Jan. 18, 2022

(65) Prior Publication Data

US 2022/0225971 A1 Jul. 21, 2022

Related U.S. Application Data

(60) Provisional application No. 63/139,180, filed on Jan. 19, 2021.

(51) Int. Cl.
*A61B 10/02* (2006.01)

(52) U.S. Cl.
CPC ...... *A61B 10/0275* (2013.01); *A61B 10/0283* (2013.01)

(58) Field of Classification Search
CPC ........ A61B 10/0275; A61B 2010/0208; A61B 10/0266; A61B 10/0283; A61B 10/0233
See application file for complete search history.

(56) References Cited

U.S. PATENT DOCUMENTS

| | | | | |
|---|---|---|---|---|
| 5,951,489 A * | 9/1999 | Bauer | A61B 10/0275 600/567 |
| 8,197,419 B2 | 6/2012 | Field et al. | |
| 10,575,832 B2 | 3/2020 | Imai et al. | |
| 10,849,601 B2 | 12/2020 | Krueger et al. | |
| 2007/0106176 A1 | 5/2007 | Mark et al. | |
| 2017/0231607 A1 | 8/2017 | Imai et al. | |
| 2018/0055493 A1* | 3/2018 | Krueger | A61B 10/0275 |
| 2018/0103939 A1 | 4/2018 | Van Liere et al. | |

FOREIGN PATENT DOCUMENTS

| | | |
|---|---|---|
| KR | 101472593 B1 | 12/2014 |
| WO | 2013158072 | 10/2013 |
| WO | 2020096812 A1 | 5/2020 |

OTHER PUBLICATIONS

International Search Report and Written Opinion dated May 9, 2022 for PCT/US2022/070233.
European Search Report dated Nov. 20, 2024 for EP22743408.1.
Extended European Search Report dated Feb. 10, 2025 for EP22743408.1.

* cited by examiner

*Primary Examiner* — Jennifer Robertson
*Assistant Examiner* — Karen E Toth
(74) *Attorney, Agent, or Firm* — Dorsey & Whitney LLP

(57) ABSTRACT

Devices and methods used to obtain a tissue sample utilizing a vacuum assist are disclosed. The devices include a handle, an inner cannula, and an outer cannula. The devices include a vacuum tube in communication with a sample notch of the inner cannula. The handle is actuated to drive the inner cannula into a lesion such that the sample notch is disposed within the lesion. A vacuum is generated in the vacuum tube and the sample notch as the stylet is driven into the lesion. A tissue sample is sucked into the sample notch and the outer cannula is displaced over the sample notch to sever the tissue sample from the lesion.

11 Claims, 12 Drawing Sheets

VACUUM-ASSISTED SOFT TISSUE BIOPSY DEVICE

RELATED APPLICATIONS

This application claims priority to U.S. Provisional Application No. 63/139,180, filed on Jan. 19, 2021 and titled, "Vacuum-Assisted Soft Tissue Biopsy Device," which is hereby incorporated by reference in its entirety.

TECHNICAL FIELD

The present disclosure relates generally to devices used to acquire a tissue sample, such as in medical devices. More specifically, in some embodiments, the present disclosure relates to devices used to acquire a soft tissue sample using a vacuum assist.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

In certain instances, a soft tissue lesion (e.g., tumor) may grow within a patient at various locations, such as breast, liver, lung, kidney, spleen, prostate, lymph nodes, etc. Sampling of a small portion of the lesion to determine the type of lesion such that a treatment regimen can be planned and implemented may be recommended to the patient. In some embodiments, the tissue sampling can be performed utilizing a biopsy device percutaneously inserted into the lesion. The biopsy device can include an inner cannula or stylet including a sample notch configured to receive a tissue sample and an outer cannula configured to sever the tissue sample from the lesion. A pathologist may desire that the tissue sample be of a minimum size (e.g., length, volume) to most effectively determine the lesion type.

Embodiments herein describe biopsy devices and methods to assist in obtaining a tissue sample of adequate size from a lesion within a patient's body. The devices can be percutaneously inserted into the lesion. In some embodiments within the scope of this disclosure, the devices include a stylet including a sample notch configured to receive a tissue sample, an outer cannula configured to sever the tissue sample from the lesion, a vacuum member in fluid communication with the sample notch, and an actuating member or handle configured to displace the stylet and outer cannula sequentially from proximal positions to distal positions either automatically or manually. The vacuum member is configured to generate a vacuum when the stylet is displaced by the actuator. The actuating member is armed by an arming slide such that the stylet and outer cannula are disposed in the proximal positions when the actuator is armed. A throw or penetration distance of the needle is adjustable by an adjustable stop member.

In use, in some embodiments within the scope of this disclosure, the biopsy device is armed by positioning the stylet and the outer cannula in proximal positions utilizing the arming slide. The stylet and the outer cannula are percutaneously inserted into the patient adjacent the lesion. The actuating member is actuated to displace the stylet into the lesion. The vacuum member generates a vacuum within the sample notch of the stylet as the stylet is displaced into the lesion. The tissue sample is sucked or drawn into the sample notch by the vacuum to increase the size of the tissue sample. The actuating member is actuated to displace the outer cannula over the stylet to sever the tissue sample from the lesion. The stylet and the outer cannula are removed from the patient. The tissue sample is removed from the sample notch.

Figure 1:
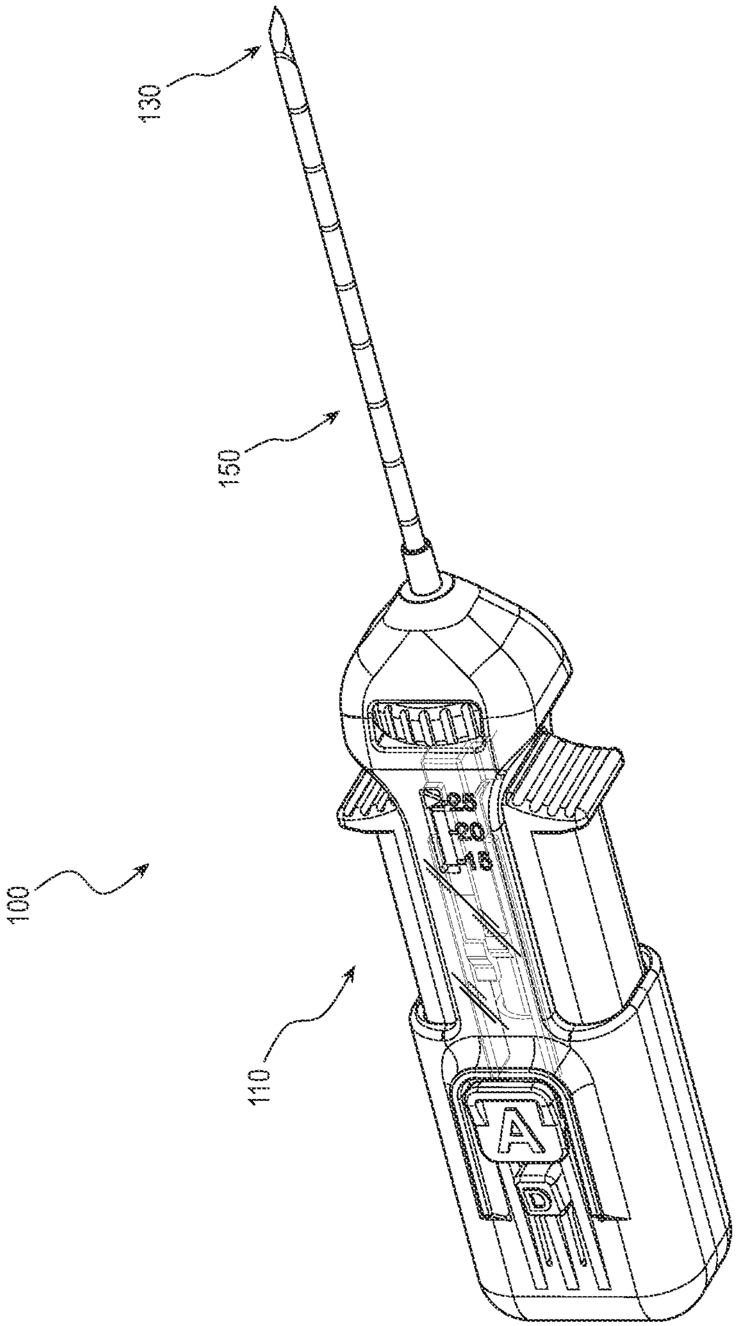
FIG. 1 is a perspective view of an embodiment of a biopsy device.
Figure 2:
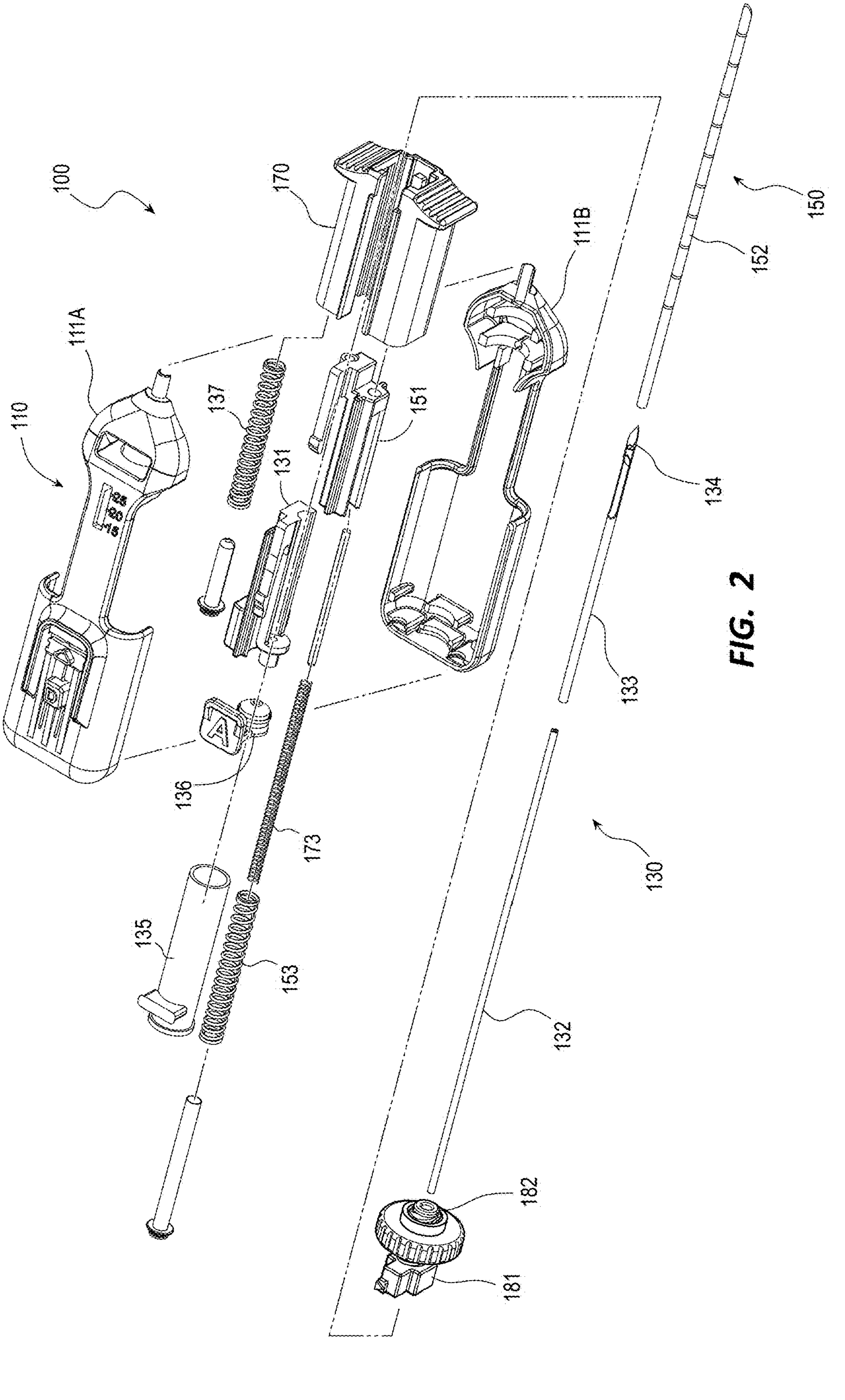
FIG. 2 is an exploded view of the biopsy device of FIG. 1.
Figure 3A:
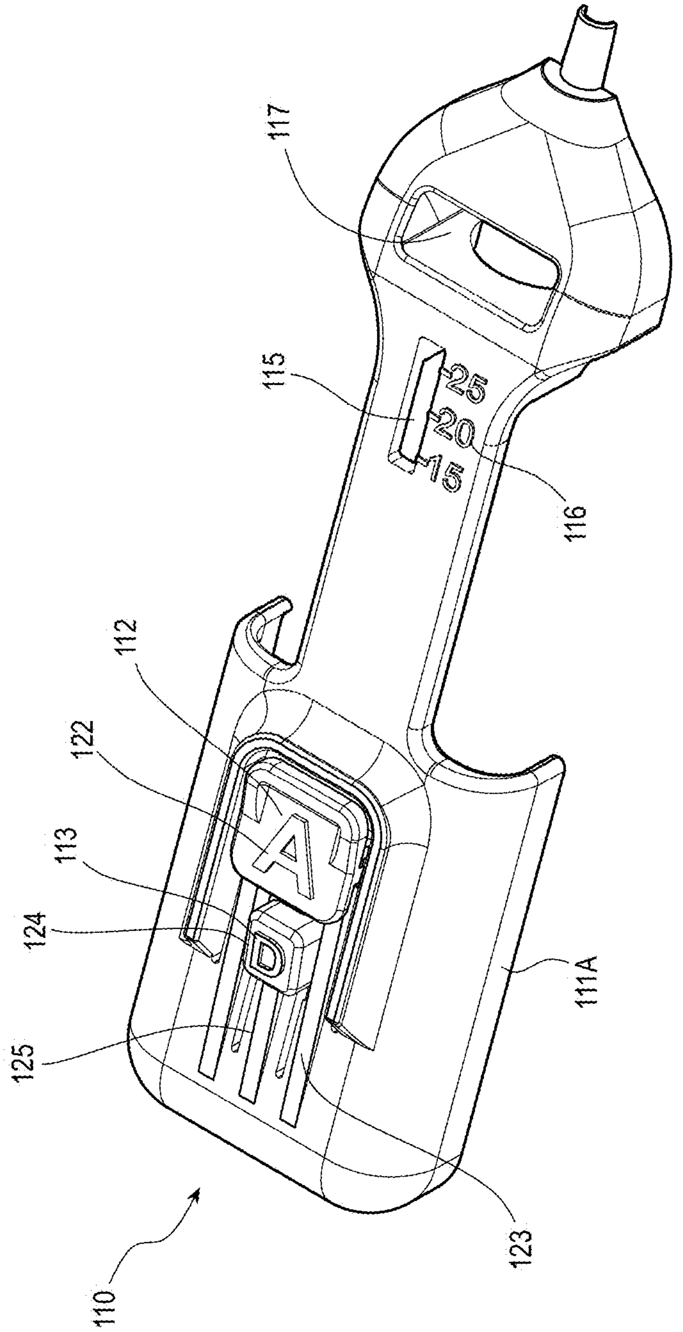
FIG. 3A is a top view of an embodiment of a top cover of the biopsy device of FIG. 1.
Figure 3B:
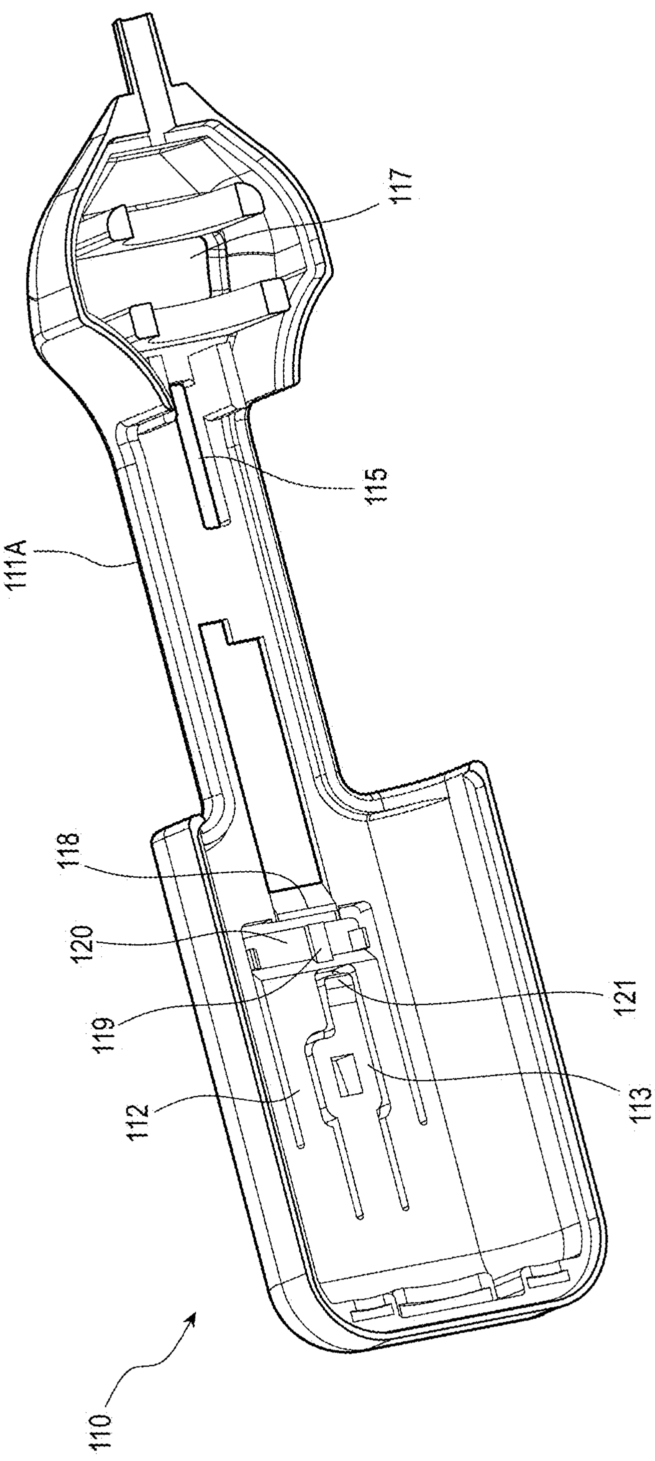
FIG. 3B is a bottom view of the top cover of FIG. 3A.
Figure 4:
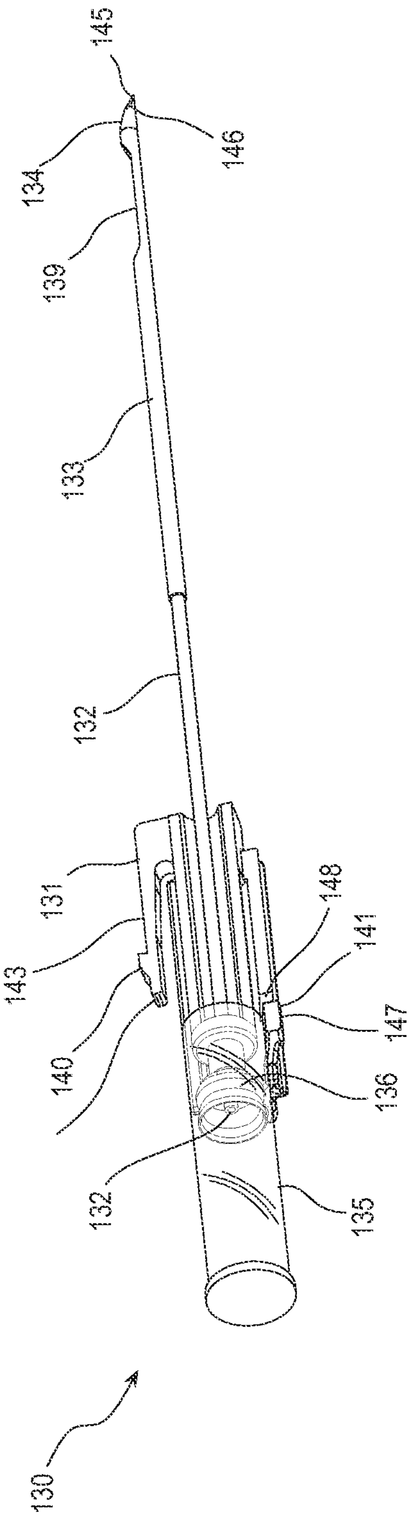
FIG. 4 is a perspective view of an embodiment of a stylet assembly including a vacuum member of the biopsy device of FIG. 1.
Figure 5:
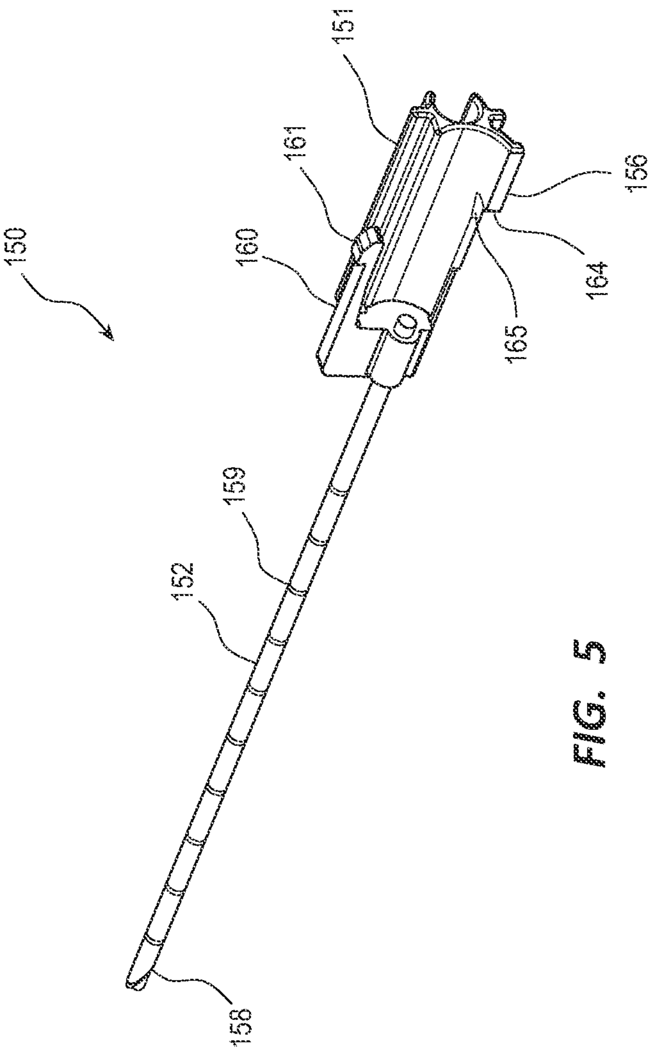
FIG. 5 is a perspective view of an embodiment of a cutting cannula assembly of the biopsy device of FIG. 1.
Figure 6:
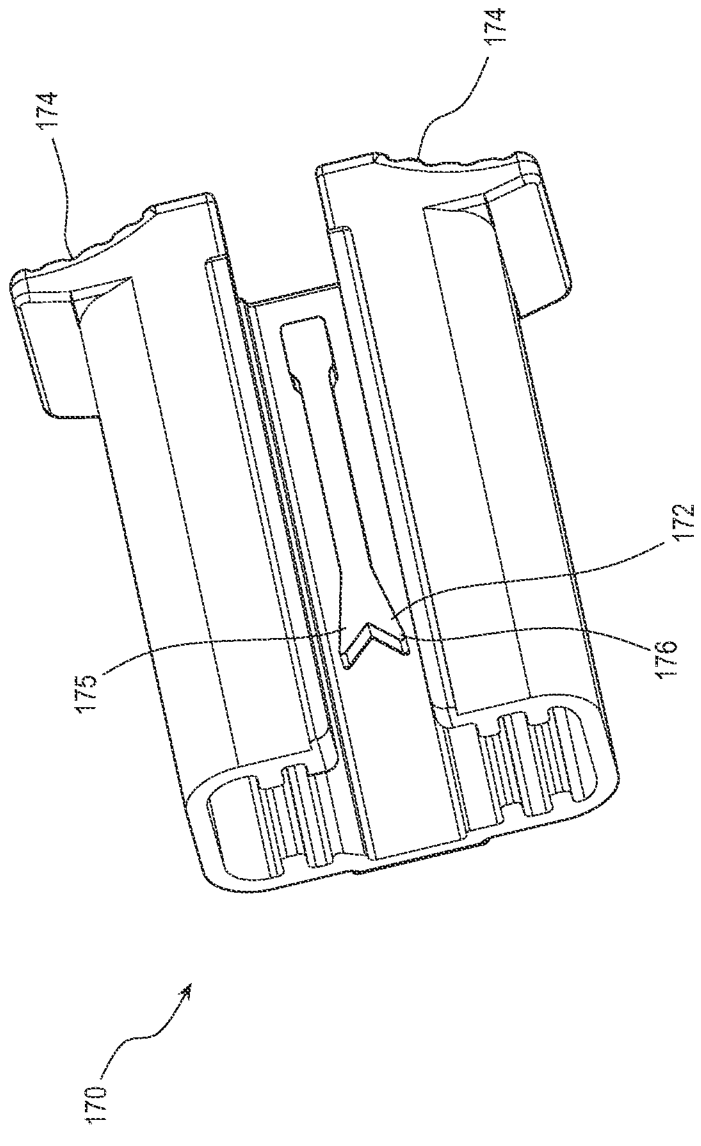
FIG. 6 is a perspective view of an embodiment of an arming slide of the biopsy device of FIG. 1.
Figure 7:
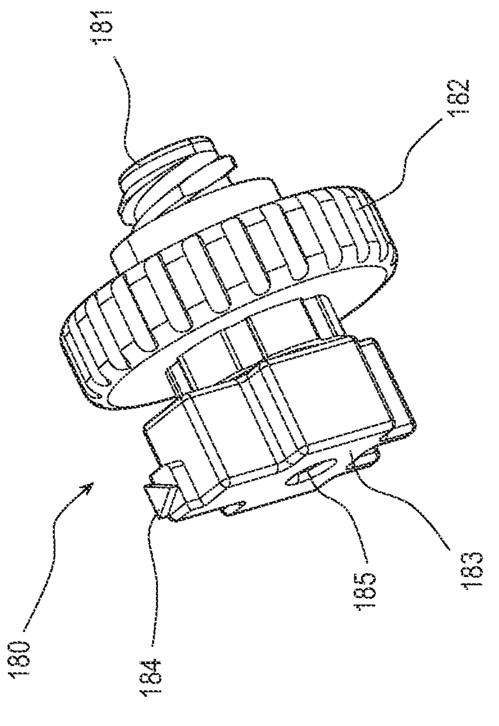
FIG. 7 is a perspective view of an embodiment of an adjustable stop member of the biopsy device of FIG. 1.

FIGS. 1 and 2 illustrate an embodiment of a biopsy device 100. FIGS. 3A and 3B illustrate an embodiment of a top shell 111A of the biopsy device 100. FIG. 4 illustrates an embodiment of a stylet assembly 130 including a vacuum member of the biopsy device 100. FIG. 5 illustrates an embodiment of a cutting cannula assembly 150. FIG. 6 illustrates an embodiment of an arming slide 170 of the biopsy device 100. FIG. 7 illustrates an embodiment of an adjustable stop or penetration depth member 180 of the biopsy device. FIGS. 8A-8D illustrate the biopsy device 100 in one embodiment of use. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 illustrates an embodiment of a biopsy device 100. As illustrated in FIG. 1, the biopsy device 100 includes three broad groups of components; each group may have numerous subcomponents and parts. The three broad component groups are: a handle 110, a stylet assembly 130, and a cutting cannula assembly 150. The biopsy device 100 can be configured to obtain a soft tissue sample from a lesion with vacuum assistance.

FIG. 2 illustrates an exploded view of the biopsy device 100. As illustrated in FIG. 2, the handle 110 can include a top shell 111A, a bottom shell 111B, an arming slide 170, a return spring 173, and the adjustable stop member 180 including a threaded stop 181, and an adjustment wheel 182.

The stylet assembly 130 may include a stylet hub 131, a proximal stylet cannula 132, a distal stylet cannula 133, a trocar tip 134, a vacuum tube 135, a piston 136, a stylet drive spring 137, and a stylet spring guide 138. The cutting cannula assembly 150 can include a cutting cannula hub 151, a cutting cannula 152, a cutting cannula drive spring 153, and a cutting cannula spring guide 154.

FIG. 3A illustrates a top view of the top shell 111A and FIG. 3B illustrates a bottom view of the top shell 111A of the handle 110. As illustrated in FIG. 3A, the top shell 111A can include a first actuator 112 and a second actuator 113. The first actuator 112 may include a first button 122 disposed at an end of a first cantilever arm 123. The first button 122 can include an indicium, such as the letter "A" indicating an "automatic" mode of operation. Other indicia are contemplated. The second actuator 113 may include a second button 124 disposed at an end of a second cantilever arm 125. The second button 124 can include an indicium, such as the letter "D" indicating a "delayed" mode of operation. Other indicia are contemplated. The actuators 112, 113 can be depressed by a user to actuate the biopsy device 100 as will be discussed below. The cantilever arms 123, 125 may return the actuators 112, 113 from an actuated state to a ready state.

As further illustrated in FIG. 3A, the top shell 111A may include a penetration depth window 115 disposed through the top shell 111A. Penetration depth indicia 116 can be disposed adjacent the penetration depth window 115. The penetration depth indicia 116 may include one or more numbers to indicate a desired penetration depth in millimeters. For example, in the illustrated embodiment, the penetration depth indicia 116 include the numbers 15, 20, and 25 indicating desired penetration depths of 15 millimeters, 20 millimeters, and 25 millimeters, respectively, and any length therebetween. A wheel window 117 can be disposed through the top shell 111A adjacent a distal end of the top shell 111A. The wheel window 117 can be configured to allow the adjustment wheel 182 to extend through the wheel window 117.

As illustrated in FIG. 3B, the top shell 111A can include a stationary shoulder or catch 118 distending from an inner surface configured to engage with trigger catches of the stylet hub 131 and the cutting cannula hub 151. The stationary shoulder 118 can include a proximally directed face oriented substantially perpendicular to a longitudinal axis of the top shell 111A. In certain embodiments, the proximally directed face may be angled at about 10 degrees relative to a longitudinal axis of the top shell 111A. The first actuator 112 can include a first recess 119 and a second recess 120, both recessed from an inner surface of the first actuator 112. The first recess 119 is configured to engage with the trigger catch of the stylet hub 131 and the second recess 120 is configured to engage with the trigger catch of the cutting cannula hub 151. A depth of the first recess 119 is less than a depth of the second recess 120 wherein the first recess 120 can engage the trigger catch of the stylet hub 131 before engaging the trigger catch of the cutting cannula hub 151. This configuration allows the stylet hub 131 to be fired before or prior to the firing of the cutting cannula hub 151. The second actuator 113 can include a protrusion 121 distending downwardly from the second actuator 113 and configured to engage with an actuator tab of the stylet hub 131 to fire the stylet hub.

FIG. 4 illustrates an embodiment of the stylet assembly 130. As illustrated in FIG. 4, the stylet assembly 130 can include the stylet hub 131, the proximal stylet cannula 132, the distal proximal stylet cannula 133, the trocar tip 134, the vacuum tube 135, and the piston 136. The stylet hub 131 can include a cantilever arm 143. The cantilever arm 143 may include a trigger catch 140 and an actuator tab 144. The trigger catch 140 may include a distally directed face configured to engage with the proximally directed face of the stationary shoulder 118. When engaged, the stylet hub 131 can be retained in a proximal position. The actuator tab 144 can extend proximally from the trigger catch 140. The trigger catch 140 can be engaged by the first protrusion 119 when the first actuator 112 is depressed and the actuator tab 144 can be engaged by the third protrusion 121 when the second actuator 113 is depressed. When the trigger catch 140 and/or the actuator tab 144 are engaged, the cantilever arm 143 may be deflected downwardly causing the trigger catch 140 to disengage from the stationary shoulder 118 allowing the stylet hub 131 to be driven distally by the stylet drive spring 137. A load catch 141 can be disposed on a bottom surface of the stylet hub 131. The load catch 141 may include an angled finger 147 and an angled slot 148.

The proximal stylet cannula 132 can be a cylindrical tube with a lumen extending therethrough. The proximal stylet cannula 132 may be fixedly coupled to the stylet hub 131 and a proximal end may extend through the piston 136 into the vacuum tube 135 such that the lumen is in fluid communication with the vacuum tube 135. The distal stylet cannula 133 can be a cylindrical tube with a lumen extending therethrough. The distal stylet cannula 133 can be co-axially disposed over a distal portion of the proximal stylet cannula 132 such that the lumen of the distal stylet cannula 133 is in fluid communication with the lumen of the proximal stylet cannula 132 and the vacuum tube 135. The proximal stylet cannula 132 and the distal stylet cannula 133 can be fixedly coupled using any suitable technique, such as welding, gluing, and frictional fit. Other techniques are contemplated. In other embodiments, the proximal and distal stylet cannulae 132, 133 may be a stylet cannula of a unibody construct.

A sample notch 139 may be disposed in the distal stylet cannula 133 adjacent a distal end and configured to receive a tissue sample. The sample notch 139 can have a length ranging from about 19 millimeters to about 22 millimeters and a depth ranging from about 50% to about 80% of a diameter of the distal stylet cannula 133. The sample notch 139 may be in fluid communication with the vacuum tube 135 through the lumens of the proximal and distal stylet cannulae 132, 133.

The trocar tip 134 may be disposed at the distal end of the distal stylet cannula 133. The trocar tip 134 can be at least partially disposed within the lumen of the distal stylet cannula 133. The trocar tip 134 may be fixedly coupled to the distal stylet cannula 133 utilizing any suitable technique. For example, the technique can include welding, gluing, and friction fit. Other techniques are contemplated within the scope of this disclosure. The trocar tip 134 can include a sharp point 145 and sharp facets 146 configured to penetrate and cut tissue.

A vacuum member such as vacuum tube 135 can be disposed adjacent a proximal end of the stylet hub 131. In some embodiments, a proximal end of the stylet hub 131 may extend into the vacuum tube 135. The vacuum tube 135 may include a cylindrical tube having a closed proximal end, an open distal end, and a bore extending therebetween. The piston 136 can be slidingly disposed within the bore and can be configured to seal against an inner surface of the vacuum tube 135. The piston 136 may be formed of a compliant material, such as rubber, latex, and thermoplastic elastomer. Other materials are contemplated, such as a rigid plastic piston with a compliant O-ring. The distal end of the proximal stylet cannula 132 can extend through the piston 136 into the bore of the vacuum tube 135 wherein the lumen of the proximal stylet cannula 132 is in fluid communication with the bore. The piston 136 may be fixedly coupled to the stylet hub 131. When the stylet hub 131 is proximally translated, the vacuum tube 135 is stationary relative to the handle 110 and the piston 136 is proximally translated within the bore of the vacuum tube 135 causing air within the vacuum tube 135 to be expelled through the sample notch 139. When the stylet hub 131 is distally translated, the vacuum tube 135 is stationary relative to the handle 110 and the piston 136 is distally translated within the bore of the vacuum tube 135 to generate a vacuum within the bore proximal to the piston 136 and within the sample notch 139.

FIG. 5 illustrates an embodiment of the cutting cannula assembly 150. As illustrated, the cutting cannula assembly 150 can include the cutting cannula hub 151 and the cutting cannula 152. The cutting cannula hub 151 can include a cantilever arm 160. The cantilever arm 160 may include a trigger catch 161. The trigger catch 161 may include a distally directed face configured to engage with the proximally directed face of the stationary shoulder 118. When engaged, the cutting cannula hub 151 can be retained in a proximal position. The trigger catch 161 can be engaged by the second protrusion 120 when the first actuator 112 is depressed. When the trigger catch 161 is engaged, the cantilever arm 160 may be deflected downwardly causing the trigger catch 161 to disengage from the stationary shoulder 118 allowing the cutting cannula hub 151 to be driven distally by the cutting cannula drive spring 153. A load catch 156 can be disposed on a bottom surface of the cutting cannula hub 151. The load catch 156 may include an angled finger 164 and an angled slot 165.

The cutting cannula 152 can be fixedly coupled to the cutting cannula hub 151 and co-axially disposed over the proximal and distal stylet cannulae 132, 133. The cutting cannula 152 can include a cylindrical tube with a lumen extending therethrough. A distal end 158 of the cutting cannula 152 can be beveled wherein the distal end 158 may sever a tissue sample from a lesion when the cutting cannula 152 is translated over the sample notch 139. The cutting cannula 152 may include marker bands 159 disposed along a length of the cutting cannula 152. The marker bands 159 can be equally spaced to indicate an insertion depth of the cutting cannula 152. For example, a distance between the marker bands 159 can be one centimeter. Other distances are contemplated. Further, the marker bands 159 may reflect ultrasound energy wherein a location of the cutting cannula 152 can be determined using ultrasound imaging techniques.

FIG. 6 illustrates an embodiment of the arming slide 170. As illustrated, the arming slide 170 can include a hub catch 172 and a finger grip 174. The arming slide 170 may be slidingly disposed over or within portions of the top and bottom shells 111A, 111B to arm the biopsy device 100. The hub catch 172 can be disposed within the arming slide 170 and extend upward from an inner surface. The hub catch 172 may include a V-shape having two catches, a stylet hub catch 175 and a cannula hub catch 176, extending angularly away from one another from a central axis of the hub catch 172. The stylet hub catch 175 can be configured to engage the load catch 141 of the stylet hub 131 wherein the stylet hub catch 175 is received within the angled slot 148. The cannula hub catch 176 can be configured to engage the load catch 156 of the cutting cannula hub 151 wherein the cannula hub catch 176 is received within the angled slot 165. When the hub catches 175, 176 are received within the angled slots 148, 165, the hubs 131, 151 can be displaced proximally by the arming slide 170 to arm the biopsy device 100.

The finger grips 174 may be disposed at a distal end of the arming slide 170. The finger grips 174 can be grasped by fingers of the user to proximally displace the arming slide 170 when arming the biopsy device 100. The finger grips 174 may include grip-enhancing features, such as ribs, grooves, bumps, dimples, a textured surface, and a compliant surface. Other grip-enhancing features are contemplated. The arming slide 170 may be returned to a distal position by a distally directed force applied by the return spring 173. The return spring 173 can be co-axially disposed within the cutting cannula drive spring 153.

FIG. 7 illustrates an embodiment of the adjustable stop member 180 configured to facilitate adjustment of the needle penetration depth. As illustrated, the adjustable stop member 180 can include the threaded stop 181 and the adjustment wheel 182 threadingly coupled with the threaded stop 181. The threaded stop 181 may include male threads disposed adjacent a distal end and configured to engage with female threads of the adjustment wheel 182. A proximally facing stop surface 183 can be disposed at a proximal end of the threaded stop 181. The stop surface 183 may be configured to interface with distal ends of the hubs 131, 151 to stop distal movement of the hubs 131, 151 when the biopsy device 100 is actuated. A bore 185 may extend through the threaded stop 181 for passage of the cutting cannula 152. An indicium 184 can be disposed on an upper surface of the threaded stop 181. In the illustrated embodiment, the indicium 184 is an arrow. In other embodiments, other indicia are contemplated. The indicium 184 may be disposed within the penetration depth window 115 of the top shell 111A to indicate a desired depth of needle penetration.

The adjustment wheel 182 may include grip-enhancing features to improve handling of the adjustment wheel 182 when an adjustment of a desired penetration depth is made. The grip-enhancing features may include ribs, grooves, bumps, dimples, a textured surface, and a compliant surface. Other grip-enhancing features are contemplated. The adjustment wheel 182 can be disposed through the wheel window 117 of the top shell 111A and a wheel window of the bottom shell wherein the adjustment wheel 182 can be rotated by the user. When the adjustment wheel 182 is rotated, the threaded stop 181 is axially translated to adjust a stop position of the hubs 131, 151 and the depth of needle penetration.

Figure 8A:
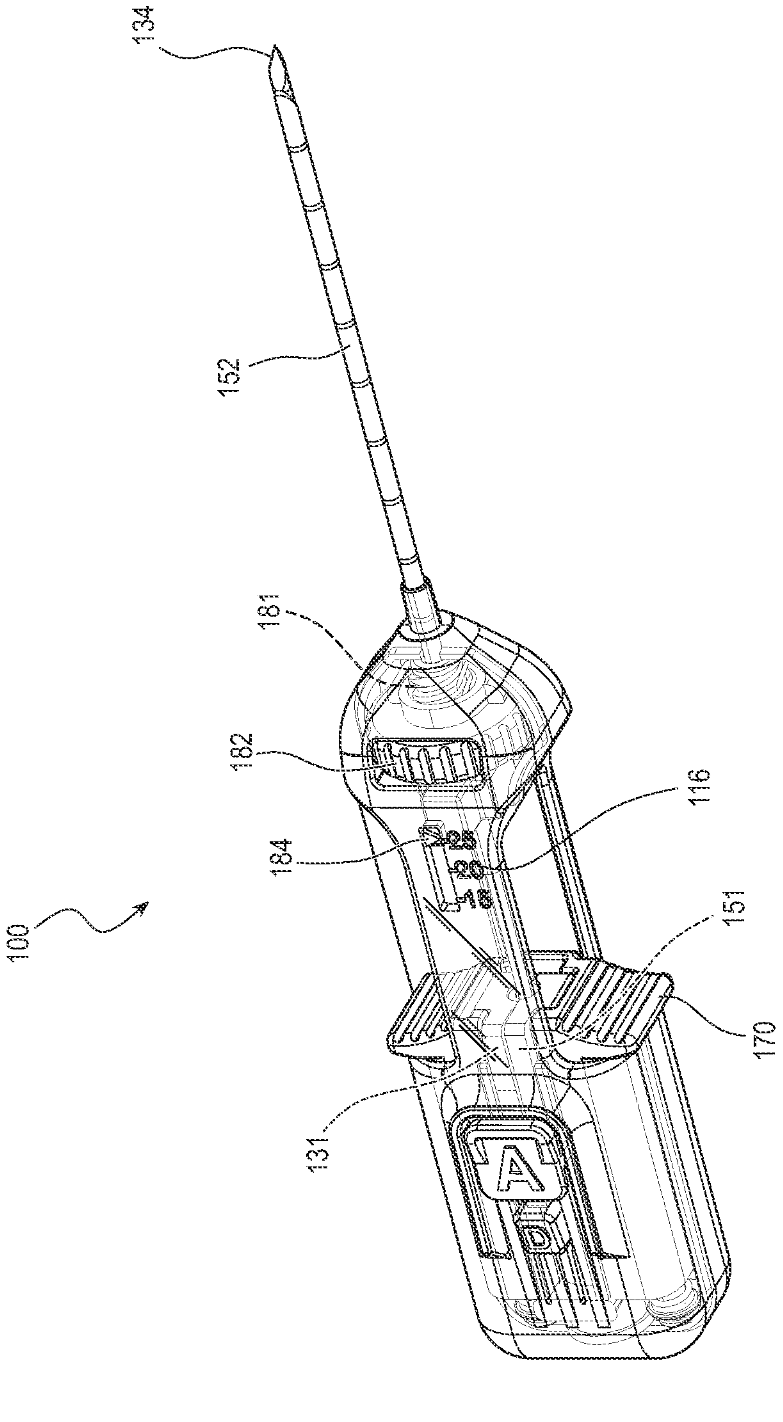
FIG. 8A is a perspective view of the biopsy device of FIG. 1 in an armed state.

In use, the biopsy device 100 may be utilized to obtain a tissue sample, such as a soft tissue sample of a lesion located in the breast, liver, lung, kidney, spleen, prostate, or lymph nodes of a patient. The lesion can be a tumor or any other type of soft tissue malformation. FIGS. 8A-8D illustrate the biopsy device 100 during an embodiment of a use within the scope of this disclosure. As illustrated in FIG. 8A, the biopsy device 100 may be loaded or armed when the arming slide 170 is gripped by the user to displace the arming slide 170 proximally. As the arming slide 170 is translated proximally a first time, the cutting cannula hub 151 can engage the arming slide 170 when the cannula hub catch is received within the angled slot as previously described. The cutting cannula hub 151 can be translated proximally to a proximal position in an armed state wherein the cannula drive spring is compressed. Tactile, visual, and/or audible feedback may be provided to the user to indicate that the cutting cannula hub 151 is in the armed state. The cutting cannula hub 151 may be retained in the proximal position by engagement of the stationary shoulder and the trigger catch as previously described. Proximal displacement of the cutting cannula hub 151 causes the cutting cannula 152 to be translated proximally. The arming slide 170 can be released to return to the distal position by a distally directed force applied by the return spring.

In some embodiments, the arming slide 170 may be gripped again by the user and translated proximally a second time. As the arming slide 170 is translated proximally a second time, the stylet hub 131 may be engaged by the arming slide 170 when the stylet hub catch is received within the angled slot. The stylet hub 131 can be translated proximally to a proximal position in an armed state wherein the stylet drive spring is compressed. Tactile and/or audible feedback may be provided to the user to indicate that the stylet hub 131 is in the armed state. The stylet hub 131 may be retained in the proximal position by engagement of the stationary shoulder and the trigger catch as previously described. Proximal displacement of the stylet hub 131 causes the proximal and distal stylet cannulae 132, 133 to be translated proximally. Further, when the stylet hub 131 is displaced proximally, the piston 136 may be translated proximally within the vacuum tube and the air within the vacuum tube can be expelled through the sample notch. In certain embodiments, a desired penetration depth can be set when the adjustment wheel 182 is rotated to adjust a position of the threaded stop 181 as indicated by the position of the indicium 184 in relation to the penetration depth indicia 116.

Figure 8B:
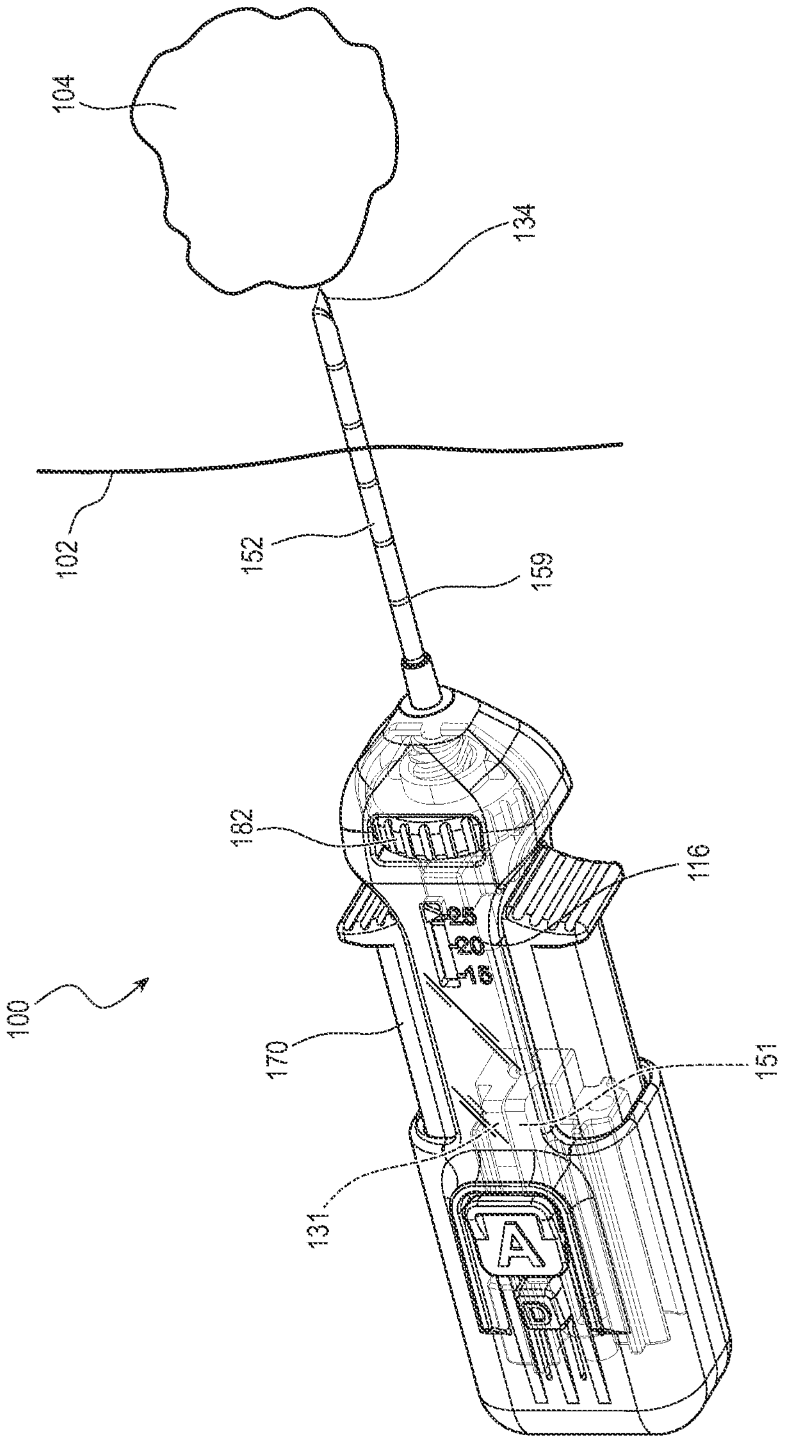
FIG. 8B is a perspective view of the biopsy device of FIG. 1 inserted through the skin of a patient and adjacent a lesion.

As illustrated in FIG. 8B, the arming slide 170 may be translated distally by the distally directed force applied to the arming slide 170 by the return spring. The trocar tip 134 and the cutting cannula 152 can be inserted through a patient's skin 102 and positioned adjacent a lesion 104. In another embodiment, the trocar tip 134 and the sample notch may be positioned within the lesion 104. In some embodiments, the marker bands 159 of the cutting cannula 152 can be utilized as a depth reference to determine an insertion depth of the cutting cannula 152. In other embodiments, the marker bands 159 may be utilized in conjunction with ultrasound imaging to determine a position of the cutting cannula 152 relative to the lesion 104.

Figure 8C:
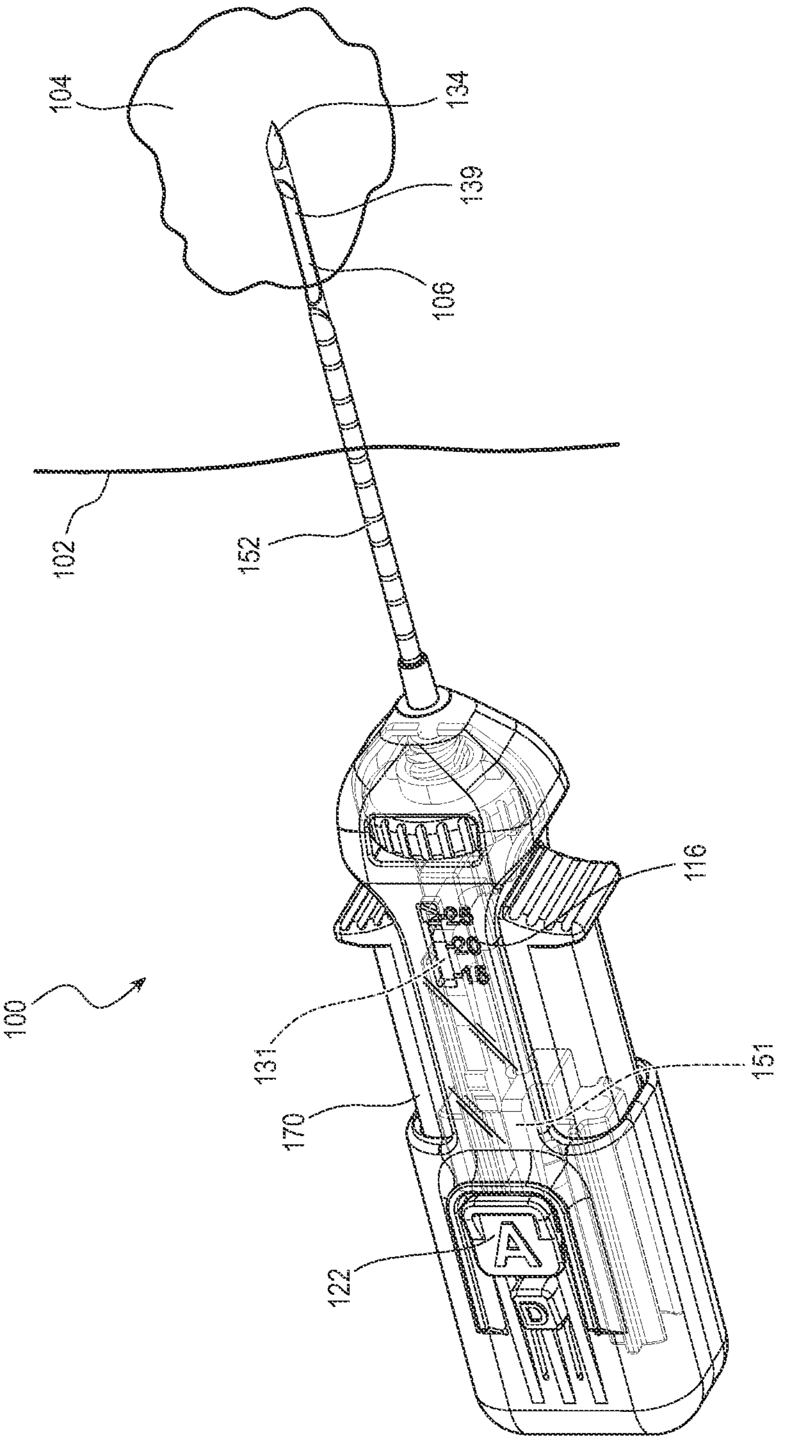
FIG. 8C is a perspective view of the biopsy device of FIG. 1 wherein the stylet is driven into the lesion and a tissue sample is sucked into a sample notch.

As illustrated in FIG. 8C, in certain embodiments, the first button 122 can be depressed such that the first protrusion engages the stylet hub trigger catch to disengage the stylet hub trigger catch from the stationary shoulder. When disengaged, the stylet hub 131 can be driven distally by the stylet drive spring until the stylet hub 131 impacts the threaded stop 183. The trocar tip 134 can penetrate the lesion 104 and the sample notch 139 may be disposed within the lesion 104. When the stylet hub 131 is driven distally, the piston 136 can be displaced distally within the vacuum tube creating a vacuum within the vacuum tube and the sample notch 139. In other words, the vacuum within the vacuum tube and the sample notch can 139 be generated while the sample notch 139 is displaced distally and disposed within the lesion 104. A tissue sample 106 may be drawn or sucked into the sample notch 139 by the vacuum. The vacuum can facilitate fully filling the sample notch 139 with the tissue sample 106 resulting in an increase in size (e.g., volume) of the tissue sample 106 when compared to a non-vacuum-assisted biopsy procedure.

Figure 8D:
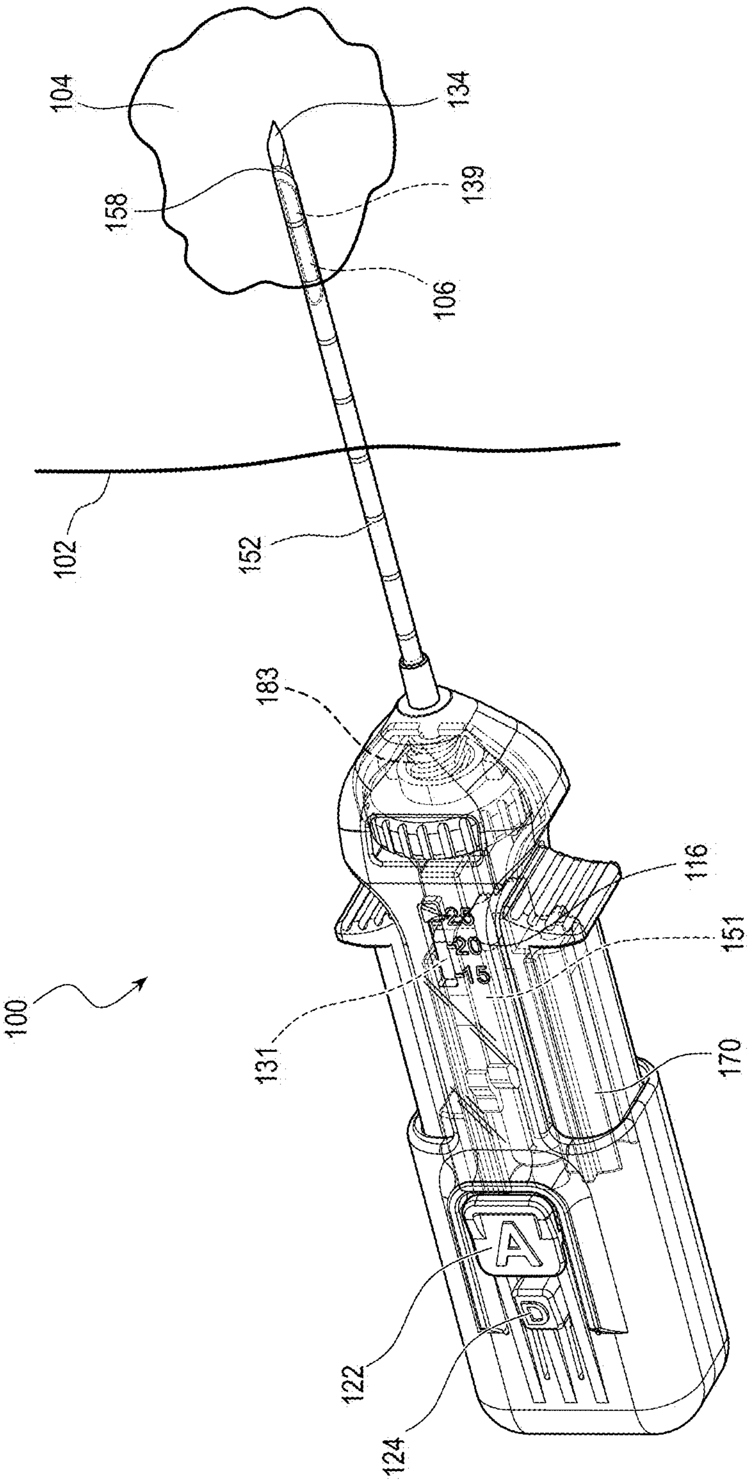
FIG. 8D is a perspective view of the biopsy device of FIG. 1 wherein the cutting cannula is displaced over the sample notch to sever the tissue sample from the lesion.

As illustrated in FIG. 8D the first button 122 can be further depressed such that the second protrusion engages the cutting cannula hub trigger catch to disengage the cutting cannula hub trigger catch from the stationary shoulder. When disengaged, the cutting cannula hub 151 can be driven distally by the cannula drive spring until the cutting cannula hub 151 impacts the threaded stop 183. In other words, the stylet assembly and the cutting cannula assembly can be automatically, sequentially actuated via depression of the first button 122. The sequential actuation is due to the difference in the heights of the first protrusion and the second protrusion. Said another way, the trigger catch of the stylet hub is disengaged from the stationary shoulder by the taller first protrusion prior to the disengagement of the trigger catch of the cutting cannula hub from the stationary shoulder by the shorter second protrusion. When the cutting cannula hub 151 is driven distally, the cutting cannula 152 is displaced over the sample notch 139 wherein the beveled end 158 severs the tissue sample 106 disposed within the sample notch 139 from the lesion 104. Following severing of the tissue sample 106, the cutting cannula 152 can cover the tissue sample 106 disposed within the sample notch 139 to retain the tissue sample 106 within the sample notch 139.

In another embodiment, the second button 124 can be depressed to engage the actuator tab to disengage the first protrusion from the stationary shoulder. When disengaged, the stylet hub 131 may be driven distally by the stylet drive spring. Following distal displacement of the stylet hub 131, the first button 122 can be depressed to disengage the second protrusion from the stationary shoulder and allow the cutting cannula hub 151 to be driven distally by the cannula drive spring.

When the stylet hub 131 and/or the cutting cannula hub 151 are driven proximally and stopped by the threaded stop 183, a loud noise is created by the impact. The loud noise may be disturbing to the user and/or a patient. In some embodiments, the vacuum generated by the biopsy device 100 when the stylet hub 131 is driven distally can dampen the impact noise of the stylet hub 131 impacting the threaded stop 183.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of obtaining a tissue sample may include one or more of the following steps: arming a tissue sampling device; inserting an inner cannula and an outer cannula into a patient and positioning the inner cannula and outer cannula adjacent a lesion; triggering displacement of the inner cannula from a position adjacent the lesion to a position within the lesion; generating a vacuum in a notch of the inner cannula; sucking a tissue sample into the notch; triggering displacement of the outer cannula from a position adjacent the lesion to a position within the lesion; and severing the tissue sample within the notch from the lesion. Other steps are also contemplated.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest to the practitioner during use. As specifically applied to a biopsy device of this disclosure, the proximal end of the biopsy device refers to the end nearest to the handle and the distal end refers to the opposite end, the end nearest to the trocar tip.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

The terms "a" and "an" can be described as one, but not limited to one. For example, although the disclosure may recite a housing having "a stopper," the disclosure also contemplates that the housing can have two or more stoppers.

Unless otherwise stated, all ranges include both endpoints and all numbers between the endpoints.

Recitation in the claims of the term "first" with respect to a feature or element does not necessarily imply the existence of a second or additional such feature or element.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A biopsy device, comprising:
- a shell comprising:
  - a stationary shoulder;
  - a first actuator comprising:
    - a first recess; and
    - a second recess; and
  - a second actuator comprising a protrusion;
- an arming slide disposed within the shell, the arming slide comprising a hub catch;
- a first hub comprising:
  - a first cantilever arm comprising a first trigger catch and configured to operatively engage with the stationary shoulder; and
  - a first load catch configured to engage with the hub catch;
- a second hub comprising:
  - a second cantilever arm comprising a second trigger catch configured to operatively engage with the stationary shoulder; and
  - a second load catch configured to engage with the hub catch;
- a vacuum member comprising:
  - a tube defining a vacuum chamber; and
  - a piston slidably disposed within the vacuum chamber;
- an inner cannula coupled to the first hub and in fluid communication with the vacuum chamber; and
- an outer cannula coupled to the second hub and co-axially disposed over the inner cannula.

2. The biopsy device of claim 1, wherein a depth of the first recess is less than a depth of the second recess.

3. The biopsy device of claim 1, wherein the hub catch comprises an inner cannula hub catch having a triangular shape and an outer cannula hub catch having a triangular shape.

4. The biopsy device of claim 3, wherein the first load catch is configured to receive the inner cannula hub catch and the second load catch is configured to receive the outer cannula hub catch.

5. The biopsy device of claim 1,
- wherein the piston is coupled to the first hub; and
- wherein a vacuum is generated in the vacuum chamber when the first hub is displaced from a proximal position to a distal position.

6. The biopsy device of claim 1, wherein the inner cannula comprises:
- a proximal inner cannula portion coupled to the first hub;
- a distal inner cannula portion co-axially disposed over the proximal inner cannula;

a sample notch disposed in the distal inner cannula adjacent a distal end of the inner cannula; and a trocar tip disposed in the distal end of the distal inner cannula;

wherein the sample notch is in fluid communication with the vacuum chamber and is configured to receive a tissue sample.

7. The biopsy device of claim 1, wherein the outer cannula comprises a beveled tip configured to sever a tissue sample.

8. The biopsy device of claim 1, wherein the outer cannula comprises depth markings disposed along a length of the outer cannula.

9. The biopsy device of claim 1, further comprising an adjustable penetration depth member, the adjustable penetration depth member comprising:

a threaded stop;

an adjustment wheel threadingly coupled to the threaded stop; and an indicium coupled to indicia of the shell and configured to indicate a needle penetration depth.

10. The biopsy device of claim 1, wherein the arming slide comprises:

a finger grip; and a return spring configured to return the arming slide from a proximal position to a distal position.

11. The biopsy device of claim 1, wherein the first hub further comprises a first drive spring configured to displace the first hub from a proximal position to a distal position; and wherein the second hub further comprises a second drive spring configured to displace the second hub from a proximal position to a distal position.

* * * * *